United States Patent
Gau

(10) Patent No.: US 9,274,081 B2
(45) Date of Patent: Mar. 1, 2016

(54) SAMPLE DEPENDENT SELECTION OF PARAMETERS FOR USE IN ELECTROKINETIC TREATMENT OF THE SAMPLE

(71) Applicant: GeneFluidics, Inc., Irwindale, CA (US)

(72) Inventor: Jen-Jr Gau, Pasadena, CA (US)

(73) Assignee: GeneFluidics, Inc., Irwindale, CA (US)

( * ) Notice: Subject to any disclaimer, the term of this patent is extended or adjusted under 35 U.S.C. 154(b) by 249 days.

(21) Appl. No.: 13/937,137

(22) Filed: Jul. 8, 2013

(65) Prior Publication Data

US 2014/0014531 A1    Jan. 16, 2014

Related U.S. Application Data

(60) Provisional application No. 61/741,312, filed on Jul. 16, 2012.

(51) Int. Cl.
   *G01N 27/447* (2006.01)

(52) U.S. Cl.
   CPC .................................. *G01N 27/4473* (2013.01)

(58) Field of Classification Search
   None
   See application file for complete search history.

(56) References Cited

U.S. PATENT DOCUMENTS

| | | | |
|---|---|---|---|
| 6,093,362 A * | 7/2000 | Kaltenbach et al. | 264/400 |
| 6,949,355 B2 * | 9/2005 | Yamanishi et al. | 435/34 |
| 2003/0012483 A1 * | 1/2003 | Ticknor et al. | 385/16 |
| 2007/0242105 A1 * | 10/2007 | Srinivasan et al. | 347/63 |
| 2008/0302732 A1 * | 12/2008 | Soh et al. | 210/695 |
| 2009/0011952 A1 | 1/2009 | Gau | |
| 2009/0242406 A1 * | 10/2009 | Han et al. | 204/520 |
| 2011/0027913 A1 * | 2/2011 | Bau et al. | 436/518 |

FOREIGN PATENT DOCUMENTS

WO      2011029794 A1   3/2011
WO    WO 2011/029794  *  3/2011

OTHER PUBLICATIONS

Copenheaver, Blaine R., International Search Report and Written Opinion, PCT/US2013/049619, Jan. 9, 2014, International Searching Authority, United States Patent and Trademark Office.

* cited by examiner

*Primary Examiner* — Jennifer Dieterle
(74) *Attorney, Agent, or Firm* — Gavrilovich, Dodd & Lindsey, LLP

(57) ABSTRACT

Performing an electrokinetic treatment on different samples includes identifying an electrical signal that is appropriate for use in the treatment of each sample. The identification of the electrical signals results in different electrical signals being identified for different samples. The electrokinetic treatment of a sample results in that sample being exposed to the electrical signal identified for that sample. Accordingly, different samples are exposed to different electrical signals. An electrokinetic treatment employs one or more electrokinetic phenomena to cause movement of one or more agents within the sample relative to the sample. In some instances, the method also includes using each of the electrokinetically treated samples to generate an electrochemical sample and then performing an electrochemical analysis on each of the electrochemical samples.

20 Claims, 7 Drawing Sheets

| Concentration | | | | | |
|---|---|---|---|---|---|
| | Impedance Signature | | EK treatment | | |
| Agent to be concentrated | DC Signature | AC Signature | DC Signal | AC Signal | |
| Protein$_{AX}$ | $I_{DC,1}$ | $I_{AC,1}$ | $V_{DC,1}$ | $V_{AC,1}$ | $f_{AC,1}$ |
| Protein$_{AX}$ | $I_{DC,2}$ | $I_{AC,2}$ | $V_{DC,2}$ | $V_{AC,2}$ | $f_{AC,2}$ |
| Protein$_{AX}$ | $I_{DC,3}$ | $I_{AC,3}$ | $V_{DC,3}$ | $V_{AC,3}$ | $f_{AC,3}$ |
| Protein$_{AX}$ | $I_{DC,4}$ | $I_{AC,4}$ | $V_{DC,4}$ | $V_{AC,4}$ | $f_{AC,4}$ |

Figure 3

SAMPLE DEPENDENT SELECTION OF PARAMETERS FOR USE IN ELECTROKINETIC TREATMENT OF THE SAMPLE

RELATED APPLICATIONS

This Application claims the benefit of U.S. Provisional Patent Application Ser. No. 61/741,312, filed on Jul. 16, 2012, entitled "Sample Dependent Selection of Parameters for Use in Electrokinetic Treatment of the Sample" and incorporated herein in its entirety.

FIELD

The invention relates to use of electrokinetic phenomena in preparation of samples, and more particularly, to selection of parameters for use in electrokinetic treatment of samples.

BACKGROUND

A variety of assays include using an electrochemical sensor to detect the presence and/or amount of an agent in a biological sample. Biological samples generally contain compounds in addition to the agent. These compounds are often a source of noise in the results of using the electrochemical sensor. The quality and reliability of these results can be improved by reducing this noise. The noise can be reduced by preparing a sample before using the sample with the sensor. As a result, there is a need for methods and/or system that can be used prepare samples before assays.

SUMMARY

A method includes identifying an electrical signal that is appropriate for use in an electrokinetic treatment of each one of multiple samples. The identification of the electrical signals results in different electrical signals being identified for different samples. The method also performing the electrokinetic treatment of each sample such that each sample is exposed to the electrical signal identified for that sample. The electrokinetic treatment employs one or more electrokinetic phenomena to cause movement of one or more agents within the sample relative to the sample. In some instances, the method also includes using each of the electrokinetically treated samples to generate an electrochemical sample and then performing an electrochemical analysis on each of the electrochemical samples.

In order to identify the electrical signal for one of the samples, an impedance signature for the sample can be generated and compared to data that indicates a relationship between the impedance signature of samples and the value of one or more variables of the electrical signal.

The data can be stored on a computer readable medium. Additionally, the computer readable medium can include code for a method that is executed by a computer. The method can include identifying the electrical signal that is appropriate for use in an electrokinetic treatment of each one of multiple samples.

BRIEF DESCRIPTION OF THE FIGURES

FIG. 1A is a topview of the device.

FIG. 1B is a cross section of the device shown in FIG. 1A taken along the line labeled A in FIG. 1B.

FIG. 2A is a topview of the device.

FIG. 2B is a cross section of the device shown in FIG. 2A.

FIG. 3 illustrates an example of a suitable database relating impedance signatures with the values of the variables in an electrical signal to be used in the electrokinetic treatment of a sample.

DESCRIPTION

Figure 1A:
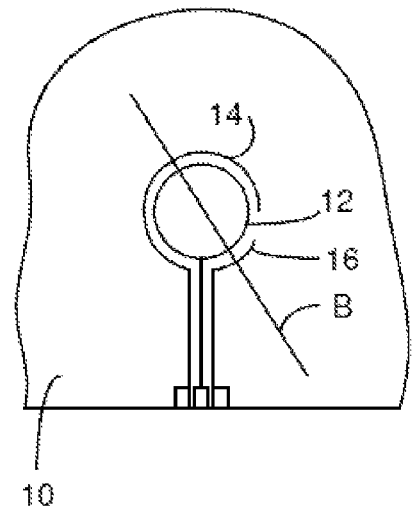
FIG. 1A and FIG. 1B illustrate a device that is suitable for performing an electrokinetic treatment of a sample.

As described above, a variety of assays employ electrochemical sensors to detect the presence and/or amount of an agent in a sample such as a biological sample. The presence of compounds other than the agent (surplus compounds) in the sample are often a source of noise in the results provided by these sensors. Preparing a sample before it is used with the sensor can reduce this noise and improve the results provided by the sensor. For instance, removing the surplus compounds can reduce this noise. Additionally or alternately, concentrating the agent in the sample can reduce this noise.

One method of sample preparation uses electrokinetics to treat the sample before using the sample with the sensor. Electrokinetics is the application of electrical fields to a sample at conditions that cause particular movement(s) of component within the sample. For instance, electrokinetics can be used to apply an electrical field to a sample that causes an agent in the sample to become concentrated at a particular location within the sample. The problem with using electrokinetics is that the electrical field that provide an effective electrokinetic treatment of a sample is different for different samples. For instance, the voltage and/or frequency that provides excellent concentration of a protein in one sample of blood may not provide an effective concentration of that same protein in a different sample of blood. This difference may result from factors that vary from different samples of blood. Examples of these factors include, but are not limited to, the difference in the viscosity, conductivity, white blood cell count, and/or protein concentration of different blood samples and/or differences in the selection and/or relative amounts of different compounds that are present in different blood samples.

The invention includes identifying different electrical signal to be used in the electrokinetic treatment of different sample. In some instances, a sample is received and an impedance analysis is performed on the sample to identify an impedance signature for the sample. The impedance signature is compared to a data that indicates a relationship between impedance signatures with the value of the variables in the electrical signal. The impedance signature for the sample is compared to the data so as to identify the proper values for the variables. An electrical signal having the identified values for the variables is then used in an electrokinetic treatment of the sample. In some instances, after the electrokinetic treatment of the sample, the electrokinetically treated sample is placed in contact with an electrochemical sensor and the electrochemical sensor is operated so as to determine the amount and/or presence of an agent in the sample.

The electrokinetic treatments applied to samples can provide different functions. For instance, in some instances, the electrokinetic treatment increases the concentration of an agent and/or one or more surplus compounds at a particular location within a sample. In some instances, the electrokinetic treatment reduces the concentration of an agent and/or one or more surplus compounds at a particular location within a sample. In some instances, the electrokinetic treatment provides mixing of the compounds in the sample. Other functions are possible. As a result, in some instances, the data is associated with a different one of the functions.

In some instances, the variable values that provide a particular function are different for particular agents. For instance, the electrokinetic parameters that concentrate a particular protein in a sample may be different from the electrokinetic parameters that concentrate a different protein in that same sample. As a result, in some instances, the data is associated with a different one of the functions and also with a particular selection of agent(s).

Figure 1B:
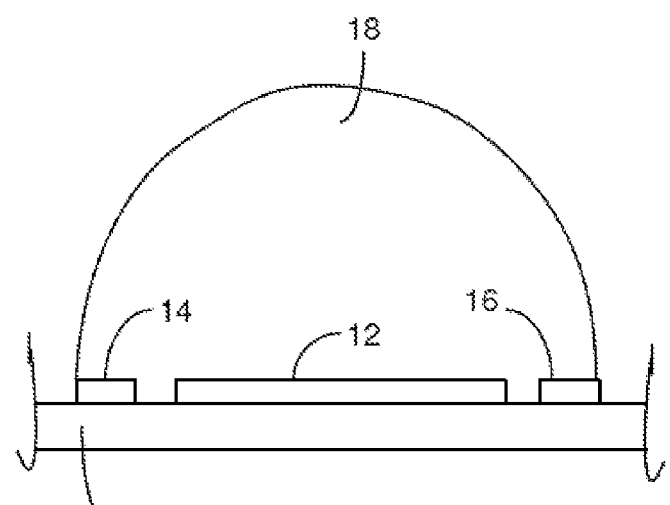

FIG. 1A and FIG. 1B illustrate a device that is suitable for performing an electrokinetic treatment of a sample. FIG. 1A is a topview of the device. FIG. 1B is a cross section of the device shown in FIG. 1A taken along the line labeled A in FIG. 1B.

The device includes electrodes on a substrate 10. The electrodes include a working electrode 12, a reference electrode 16, and an auxiliary electrode 14. In some instances, the device includes only two of the electrodes. For instance, the device can be constructed with only the working electrode 12 and a reference/auxiliary electrode. Suitable substrates 10 include, but are not limited to, nitride, cellular membrane, polymer, silicon, glass, and plastic. Suitable electrodes include or consist of a single layer of a conductive material such as a metal. In some instances, the metal is gold.

FIG. 1B illustrates a sample 18 positioned on the electrodes. In some instances, the regions of the substrate 10 outside of the electrodes are surface treated so as to be hydrophobic. The hydrophobic nature of these regions can serve to constrain the sample 18 over the electrodes. Suitable samples 18 for use with the device include, but are not limited to, blood, urine, saliva, other human specimen, buffer, food samples, cerebrospinal fluid (CSF), sputum, plasma, serum, food products, and environmental samples.

The device can be employed to perform an electrokinetic kinetic treatment on the sample 18. An electrokinetic kinetic treatment can include the application of an electrical signal to the electrodes. The electrical signal can include a periodic voltage versus time waveform such as a sinusoidal form, square waveform, triangle waveform, sawtooth waveform, or a composite waveform that is a composite of two or more different waveforms selected from a group consisting of sinusoidal form, square waveform, triangle waveform, sawtooth waveform. Such a composite waveform can be a composite of two different signals that each have the same form. For instance, the composite waveform can be a composite of two different sinusoidal waveforms. The waveform can include a DC offset or can exclude a DC offset. In some instances, the electrical signal is an AC signal on top of a DC bias (or DC offset). The electrical signal can be applied between any two of the electrodes without being applied to a third one of the electrodes. Alternately, the electrical signal can be applied between any two of the electrodes and a third one of the electrodes.

The electrokinetic treatment can be selected to perform a variety of functions on one or more agents in the sample. Examples of suitable agents include, but are not limited to, proteins, nucleic acids, DNA, RNA, ions, biological molecules, cancer cells, and pathogens, cells including human cells, small molecules, beads, and liquids. A specific example of a suitable agent is *Escherichia coli*. A specific example of a suitable agent is a pathogen.

In some instances, the electrokinetic treatment provides a mixing functionality. For instance, the electrical signal is selected to provide mixing of one or more agents in the sample. In some instances, the electrokinetic treatment provides a concentrating functionality. For instance, the electrical signal can be selected to concentrate one or more agents in the sample at or on the surface of the working electrode 12. Alternately, in some instances, the electrokinetic treatment provides a repulsion functionality. For instance, the electrical signal can be selected to repel one or more agents in the sample away from the surface of the working electrode 12. In still other instances, the electrokinetic treatment provides both a concentrating functionality and a repulsion functionality. For instance, the electrical signal can be selected to concentrate one or more first agents in the sample at or on the surface of the working electrode 12 while also repelling one or more second agents in the sample away from the surface of the working electrode 12. Although the above functionality is described in the context of moving one or more agents relative to the working electrode 12, the functionality can be selected to move one or more agents relative to one or more other electrodes.

Figure 1C:
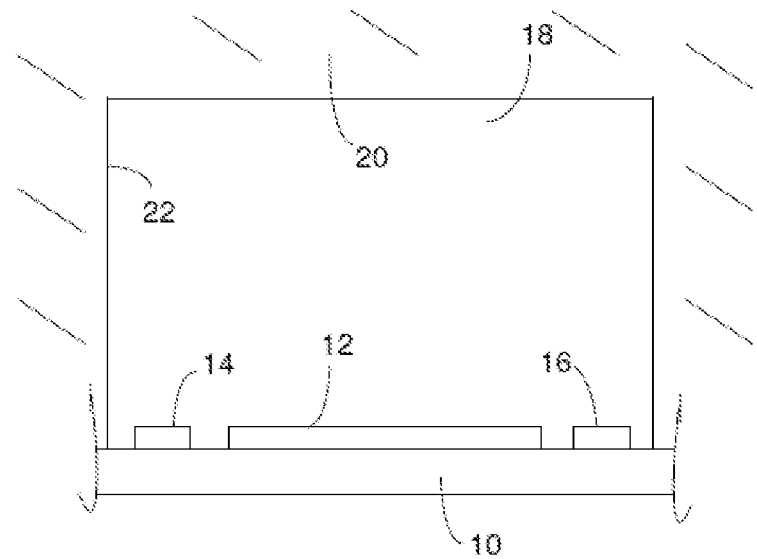
FIG. 1C is a cross section of another embodiment of the device of FIG. 1A through FIG. 1B.
Figure 1D:
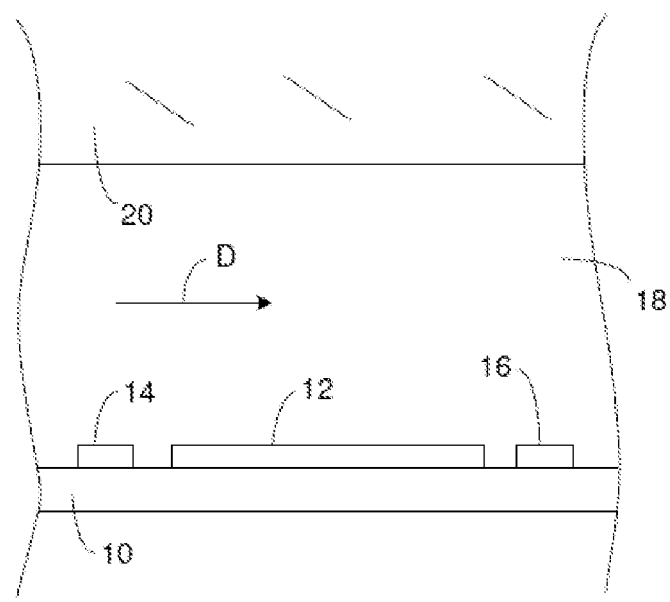
FIG. 1D is a cross section of another embodiment of the device of FIG. 1A through FIG. 1B.

FIG. 1B shows the sample 18 as a drop formed over the electrodes; however, the device can include a structure for constraining a sample over the electrodes. For instance, FIG. 1C illustrates a constraining structure 20 positioned such that a reservoir 22 that is defined by the substrate 10 and the structure is formed over the electrodes with the electrodes being located within the reservoir 22. As a result, a sample 18 positioned in the reservoir 22 is constrained within the reservoir 22 and in contact with the electrodes. Alternately, the device can be used with an open system. For instance, as shown in FIG. 1D, the sample 18 can flow over the electrodes as illustrated by the arrow labeled D.

The device of FIG. 1A through FIG. 1D can also be used as an electrochemical sensor. For instance, the device of FIG. 1A through FIG. 1D can be used to perform an electrochemical analysis that determines the amount and/or presence of an agent in a sample. An electrochemical analysis employs an applied voltage to drive and chemical reaction such as an oxidation reaction and/or oxidation reaction at the surface of the working electrode 12. The electrochemical sensor can be used in electrochemical analysis techniques (electroanalytical techniques) such as Coulometry, and voltammetry such as polarometry, amperometry, pulsing amperometry, and cyclic voltammetry.

Methods for employing the device of FIG. 1A through FIG. 1D as an electrochemical sensor, and/or for generating a sample in contact with the electrodes, and/or for transporting one or more liquids into contact with the electrodes can be found in U.S. patent application Ser. No. 12/154,971, filed on May 28, 2008, entitled "Chip Assay Having Improved Efficiency," and incorporated herein in its entirety and also in U.S. patent application Ser. No. 09/848,727, filed on May 3, 2001, entitled "Biological Identification System with Integrated Sensor Chip," and incorporated herein in its entirety and also in U.S. patent application Ser. No. 10/288,320, filed on Nov. 4, 2002, entitled "System for Detection of a Component in a Liquid," and incorporated herein in its entirety and also in U.S. patent application Ser. No. 10/702,412, filed on Nov. 5, 2003, entitled "Elevated Temperature Assay System," and incorporated herein in its entirety.

The use of a device according to FIG. 1A through FIG. 1D as an electrochemical sensor can be done after an electrokinetic treatment of the sample and without removing the sample from the device. As a result, the electrokinetic treatment can be a part of preparing the sample in place on the device. For instance, the sample upon which the electrokinetic treatment is performed and the sample upon which the electrochemical sensor functionality is employed can be the same sample. Alternately, the sample can be a preliminary sample that is used in preparing the sample upon which the electrochemical sensor functionality is employed. For instance, an electrokinetic treatment can be performed on a sample located on the electrodes. One or more additional liquids can then be added to the sample before the electrochemical sensor functionality is employed. Additionally or alternately, a portion of the sample can be removed before the electrochemical sensor functionality is employed. This ability to apply one or more electrokinetic treatment to preliminary samples generated during the preparation of the electrochemical analysis sample and/or to the electrochemical analysis sample itself increases the efficiency of the assay.

Figure 2A:
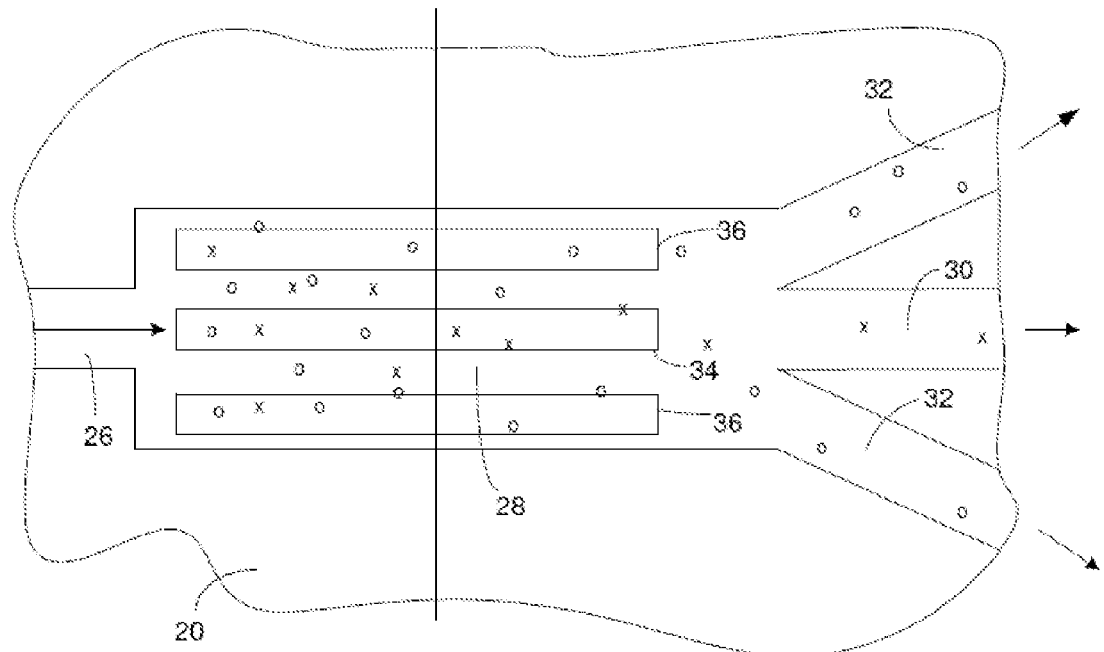
FIG. 2A and FIG. 2B illustrate another device that is suitable for use in electrokinetic treatment of a sample.
Figure 2B:
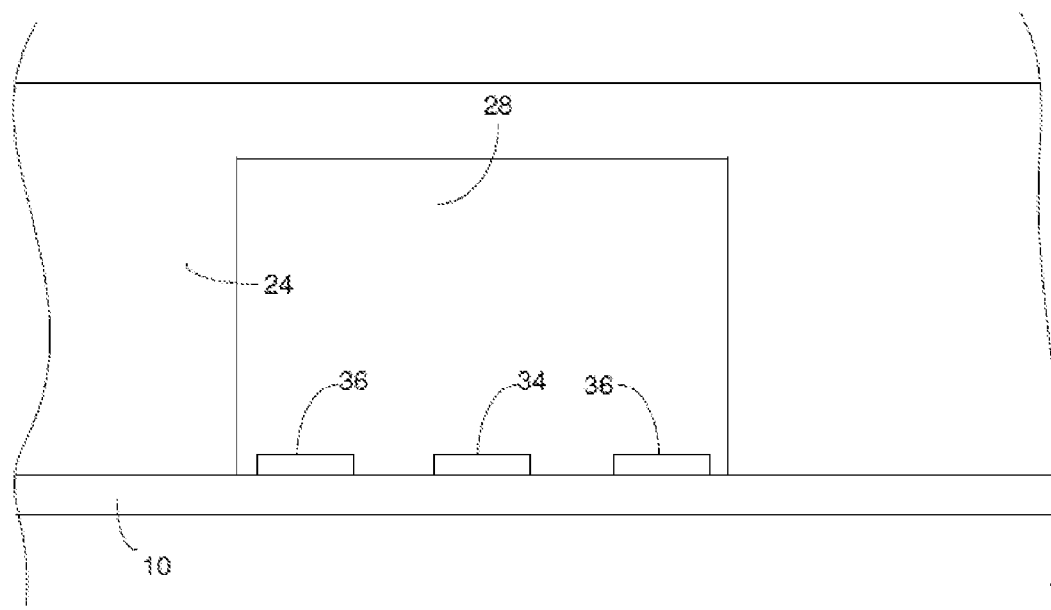

FIG. 2A and FIG. 2B illustrate another device that is suitable for use in electrokinetic treatment of a sample. FIG. 2A is a topview of the device. FIG. 2B is a cross section of the device shown in FIG. 2A. The device includes a cap 24 on a substrate 10. In FIG. 2A, the cap 24 is treated as transparent in order to make the internal features of the device visible is in the image.

The cap 24 and the substrate 10 act together to define a flow chamber within the device. The flow chamber includes an inlet 26, an electrokinetic chamber 28, and a primary outlet channel 30 between two secondary outlet channels 32. Electrodes a located in or near the electrokinetic chamber 28 such that a liquid flowing through the electrokinetic chamber 28 contacts the electrodes and/or are exposed to an electrical field that results from application of an electrical signal to the electrodes. In some instances, the electrodes include a central electrode 34 between peripheral electrodes 36.

During operation of the device, a sample flows through the electrokinetic chamber 28. Suitable samples for use with the device include, but are not limited to, blood, urine, saliva, other human specimen, buffer, food samples, cerebrospinal fluid (CSF), sputum, plasma, serum, food products, and environmental samples.

The sample flows from the inlet 26 through the electrokinetic chamber 28. Different portions of the sample flow from the electrokinetic chamber 28 and out either the primary outlet channel 30 or out one of the secondary outlet channels 32. During the electrokinetic treatment, an electrical signal is applied to the electrodes. The electrical signal can include a periodic voltage versus time waveform that is a sinusoidal form, an AC signal waveform, square waveform, triangle waveform, sawtooth waveform, or a composite waveform that is a composite of two or more different waveforms selected from a group consisting of sinusoidal form, square waveform, triangle waveform, sawtooth waveform. Such a composite waveform can be a composite of two different signals that each have the same form. For instance, the composite waveform can be a composite of two different sinusoidal waveforms. The waveform can include a DC offset or can exclude a DC offset. In some instances, the electrical signal is an AC signal on top of a DC bias (or DC offset). The electrical signal can be applied between any two of the electrodes without being applied to a third one of the electrodes. Alternately, the electrical signal can be applied between any two of the electrodes and a third one of the electrodes. For instance, the electrical signal can be applied between the central electrode 34 and each of the two peripheral electrodes 36.

As noted above, the electrical signal used in the electrokinetic treatment can be selected to perform a variety of functions on one or more agents in the sample. Examples of suitable agents include, but are not limited to, proteins, nucleic acids, DNA, RNA, ions, biological molecules, cancer cells, and pathogens, cells including human cells, small molecules, beads, and liquids. A specific example of a suitable agent is *Escherichia coli* or a pathogen.

In one example, the electrokinetic treatment can be selected such that agent is concentrated at one of the electrodes. For instance, FIG. 2B illustrates the electrical signal selected such that agents represented by the Xs are concentrated at the central electrode 34. As a result, the portion of the sample flowing out of the primary outlet channel 30 has an increased concentration of the agents labeled X relative to the portion of the sample in the inlet 26 and also relative to the portion of the sample flowing out either of the secondary outlet channels 32.

Although the above example discusses concentration of an agent at the central electrode 34, the electrical signal can be selected such that agent is concentrated at one or both of the peripheral electrodes 36. The result is an increased concentration of the agents represented by the Xs in one or both of the secondary outlet channels 32 relative to their concentration at the inlet 26 and also relative to the their concentration in the central channel.

Additionally or alternately, the electrokinetic treatment can be selected to repel an agent from one or more of the electrodes. For instance, the electrical signal can be selected to repel an agent from the central electrode 34. FIG. 2A illustrates the electrokinetic treatment selected such that agents represented by the Os are repeled by the central electrode 34. As a result, the portion of the sample flowing out each of the secondary outlet channels 32 has an increased concentration of the agents labeled O relative to the portion of the sample in the inlet 26 and also relative to the portion of the sample flowing out the primary outlet channel 30.

The above methods of operating the device of FIG. 2A can be used independently or in combination to reduce or increase the concentration of one or more first agents in the sample. Alternately, the above methods of operating the device of FIG. 2A can be used independently or in combination to increase the concentration of one or more first agents in the sample while reducing the concentration of one or more second agents in the sample. For instance, the net result of the electrokinetic functionality shown in FIG. 2 is that in the central channel the sample has an increased concentration of the agents labeled X and a decreased concentration of the agents labeled O. In contrast, the secondary channels each have an increased concentration of the agents labeled O and a decreased concentration of the agents labeled X.

After using the device of FIG. 2A through FIG. 2B to perform the electrokinetic treatment of the sample, the desired portion of the sample can then be used in an electrochemical analysis performed by a device according to FIG. 1A through FIG. 1D. For instance, the desired portion of the sample produced by the device of FIG. 2A through FIG. 2B can be used as the sample upon which the electrochemical analysis is performed or can be sued to prepare the sample upon which the electrochemical analysis is performed.

The functionalities that can be provided by the electrokinetic treatment are a result of electrokinetic phenomena. Electrokinetic phenomena are a family of several different effects that occur in heterogeneous fluids or in porous bodies filled with fluid. Since we are most interested in liquid samples, the electrokinetic phenomena at work here are lagely effects that occur in heterogeneous fluids. Heterogeneous fluids are fluid that contain particles that are solids, liquids or gas bubbles with sizes on the scale of a micrometer or nanometer. A common source of all these effects is an interfacial 'double layer' of charges. The influence of an external electric field on the diffuse layer generates tangential motion of a fluid with respect to an adjacent charged surface. As a result, electrokinetic phenomena can be used individually or combined to achieve movement of one or more agents within the sample. For instance, the electrical signal can be selected to generate a variety of different electrokinetic forces in a sample. Examples of these forces include, but are not limited to, dielectrophoretic forces, AC electroosmotic forces, DC electrophoresis, AC electrothermal forces, electrophoresis, and electrostatic forces. In the dielectrophoretic force interaction, the electrical field causes a dipole to be induced in one or more polarizable agents within the sample. When the electrical field is non-uniform, the agent experiences a net force and moves within the sample. The degree of movement can be dependent on the size of the agent, the magnitude of the electrical field gradient, and/or the conductivity of the sample. In the case of AC electroosmotic forces and AC electrothermal forces, the electrical field provided by the electrical signal tends to cause movement of the sample rather than movement of the individual particles within the sample. This movement of the sample can also contribute to the desired functionality. For instance, the electrical signal can be selected such a vortex is induced in the sample. Since particles of different sizes will move at different speeds in the vortex, the vortex causes different particles to become concentrated at different locations in the sample. AC electroosmotic forces and AC electrothermal forces tend to be longer range forces than dielectrophoretic force. The AC electroosmotic forces are less dependent on the conductivity of the sample than the AC electrothermal forces. Additionally, the AC electroosmotic forces tend to occur at lower frequencies that the AC electrothermal forces. For instance, the AC electroosmotic forces tend to occur in a range of 30 Hz-10 kHz while AC electrothermal forces tend to occur above 100 kHz and/or in a range of 300 kHz-10 MHz.

Other sources of electrokinetic forces that may be a source of movement of agent within the sample and/or of the sample itself include, but are not limited to, electrophoresis, diffusiphoresis (motion of particles under influence of a chemical potential gradient), capillary osmosis (motion of liquid in porous body under influence of a chemical potential gradient), sedimentation potential (electric field generated by sedimenting colloidal particles), streaming potential/current (either electric potential or current generated by fluid moving through porous body, or relative to flat surface), colloid vibration current (electric current generated by particles moving in fluid under influence of ultrasound), and electric sonic amplitude (ultrasound generated by colloidal particles in oscillating electric field).

One or more of the above electrokinetic forces can provide the desired functionality or the above forces can combine to provide the desired functionality. As a result, the values of the parameters (such as voltage and frequency) for a particular waveform (AC signal on top of DC signal) can be varied to identify the value of the parameters that optimize the desired functionality for a particular selection of agents within a particular sample. For instance, when it is desirable to concentrate a particular protein in a particular sample at the central electrode 34 of a device constructed according to FIG. 2A and FIG. 2B, the parameters the parameters (such as voltage and frequency) for a particular waveform (AC signal on top of DC signal) can be varied to identify the parameters that most effective result in that protein being concentrated at the central electrode 34.

The electrical signal that is effective in providing a particular functionality for the electrokinetic treatment of a particular sample is not the same for all samples. For instance, the electrical signal that is effective for concentrating a particular protein in a blood sample at a particular electrode may not be particularly effective at concentrating that same protein at the same electrode in a different sample of blood. As a result, a challenge in the successful use of electrokinetic treatments is identifying the electrical signal that is most effective at providing the desired functionality.

The Applicant has found that the electrical signal that is effective in providing a particular functionality for a particular sample is a function of an impedance signature for that sample. An impedance signature measures the sample's response to the application of an electrical current through the sample. For instance, generating the impedance signature for a sample can include applying a DC current through the sample and measuring the DC impedance of the sample or applying an AC current through the sample and measuring the AC impedance of the sample or both. As a result, data that provides a relationship between impedance signatures and the electrokinetic parameters for generating electrical signals that provide the desired functionality for particular agent(s) can be generated. This relationship can be established by a variety of methods and/or forms. For instance, the data can be a mathematical relationship between each of the different parameters and the impedance signature. Alternately, the data can be set forth in a database.

FIG. 3 illustrates an example of a suitable database relating impedance signatures with parameters for generating the electrical signal. For instance, the database associates data listed in the same row with other data in the same row. Accordingly, the database includes rows that each list one or more signature fields that together indicate the impedance signature along with one or more signal fields that together indicate parameters that can be used to generate the electrical signal.

As will be described below, the impedance signature for a sample includes data derived from one or more impedance plots of that sample. For instance, the impedance signature can include a curve from each one of one or more of the impedance plots. Additionally or alternately, the impedance signature can include a mathematical representation of the curve such as the mathematical relationship that results from performing a curve fit on the curve. Additionally or alternately, the impedance signature can include one or more mathematical features of the curve. For instance, the impedance signature can include one or more values of the curvature of the curve where each value is determined at a different location on the curve. Additionally or alternately, the impedance signature can include the value of the curve at one or more locations along the curve. Additionally or alternately, the impedance signature can include the identity of one or more features on the curve. For instance, the impedance signature can include data that showing that a maximum or minimum occurs in the curve at a particular location along the curve. Because the impedance signature can include multiple forms of data, each impedance signature shown in the database of FIG. 3 includes two fields, however the impedance signature can include a single field or more than three fields.

The one or more parameters for generating the electrical signal are the variables that define the variables in the waveform. For instance, suppose the database is associated with waveforms that are an AC signal on top of a DC signal. In this instance, the signal fields can include one or more DC fields that each lists the value of a parameter for making the DC signal and one or more AC fields that each lists the value of a parameter for making the AC signal. For instance, in FIG. 3, the one or more DC fields include a single field that lists the voltage of the DC signal. In the first row of the database in FIG. 3, the voltage of the DC signal is labeled $V_{DC,1}$ where the number 1 indicates that row number of the entry. Additionally, in FIG. 3, the one or more AC fields include a voltage field that lists the voltage of the AC signal and a frequency field that lists the frequency of the AC signal. In the first row of the database in FIG. 3, the voltage of the AC signal is labeled $V_{AC,1}$ where the number 1 indicates that row number of the entry and the frequency of the AC signal is labeled $f_{AC,1}$ where the number 1 indicates that row number of the entry.

Although FIG. 3 shows a database as providing the relationship between the impedance signatures and the parameters, as discussed above, the relationship can be in other forms such as a mathematical equation. The data in FIG. 3 can be used to generate such equations. For instance, the impedance signature can be plotted against the values of one of the parameters such as the voltage of the DC signal (labeled $V_{DC,1}$ in FIG. 3) and a curve fit performed. The mathematical equation resulting from the curve fit can serve as the expression of the relationship between the impedance signature and the parameter. As is evident from FIG. 3, several parameters are often associated with the electrical signal (FIG. 3 shows the parameters $V_{DC,i}$, $V_{AC,i}$, and $f_{AC,i}$). A mathematical equation can be generated for each of the parameters. Additionally, since the data in FIG. 3 is associated with particular functionality and agent(s), these equations will also be associated with particular functionality and agent(s).

Figure 4:
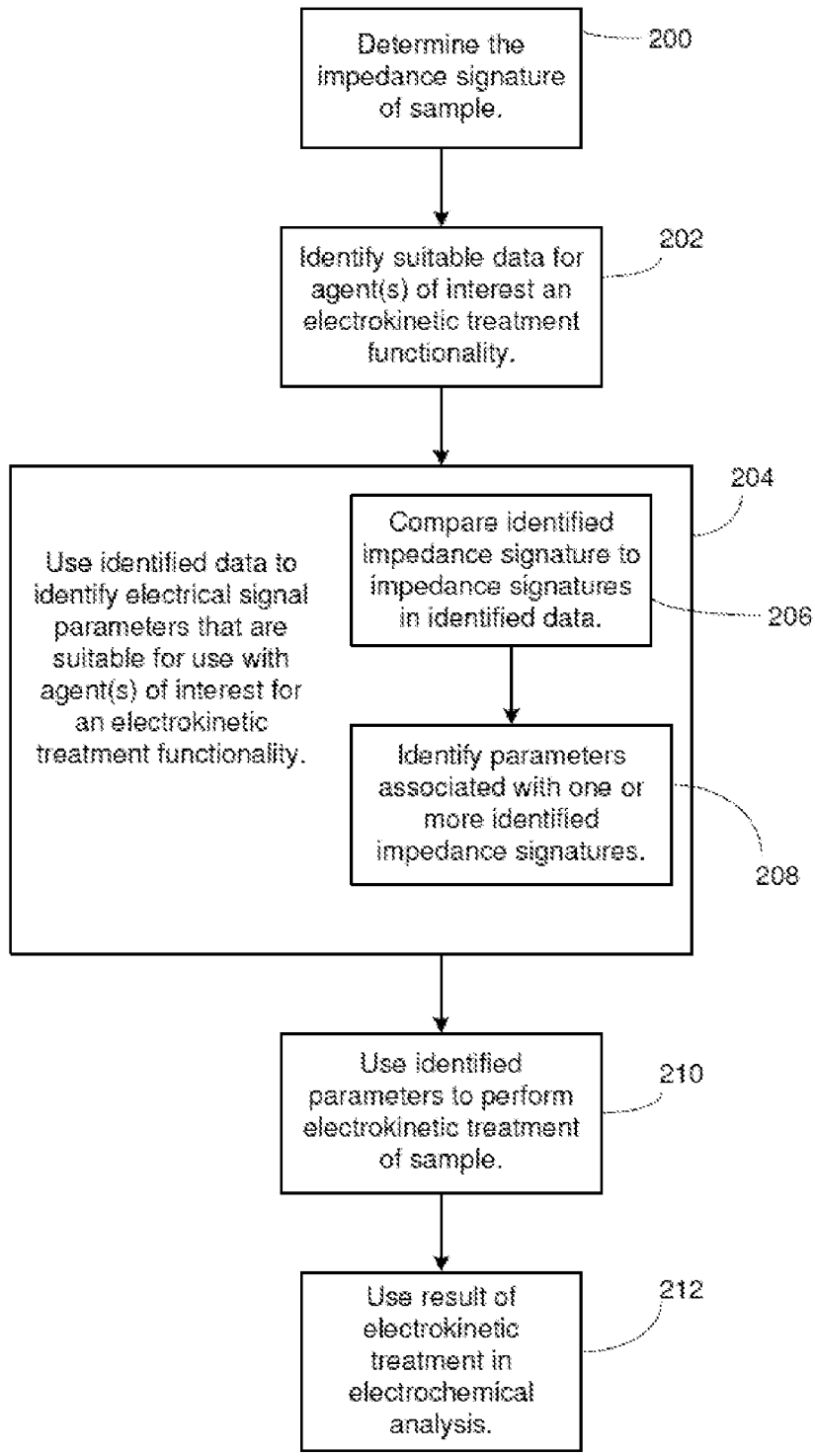
FIG. 4 illustrates a method of using impedance signature data for a sample to identify the variables of an electrical signal that is to be applied to the sample during an electrokinetic treatment of the sample.
Figure 6:
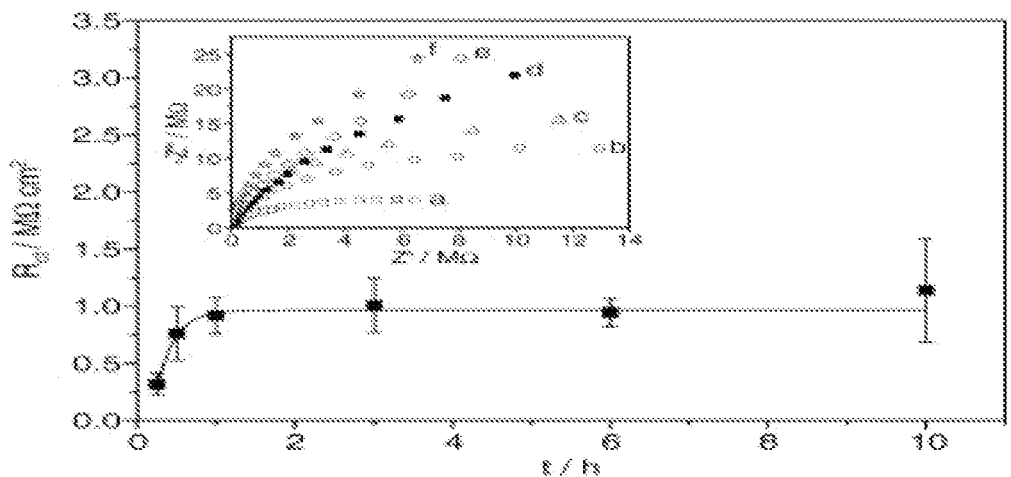
FIG. 6 illustrates a DC impedance plot.
Figure 7:
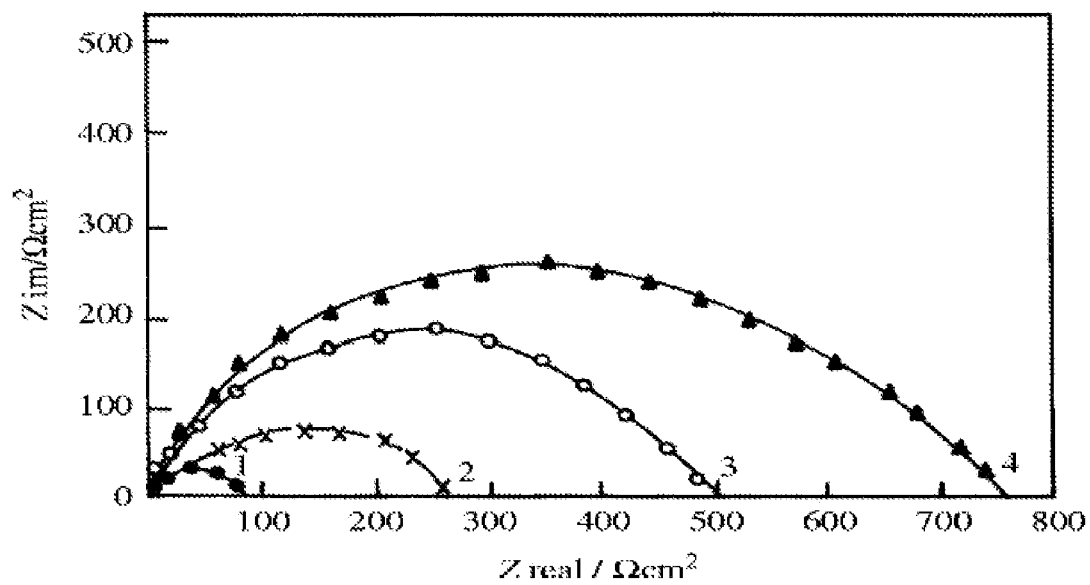
FIG. 7 illustrates an AC impedance plot.

The relationship between the impedance signatures and the parameters can be employed in performing the electrokinetic treatment of a sample. For instance, FIG. 4 illustrates a method of using the relationship to perform the electrokinetic treatment. At block 200, the impedance signature of the target sample is determined. As noted above, the impedance signature for a sample includes data derived from one or more impedance plots of that sample. Accordingly, determining the impedance signature of a sample includes generating an impedance plot for the sample. In some instances, determining the impedance signature includes generating a DC impedance plot. A DC impedance plot can be generated by applying a voltage cross the sample and measuring the resulting current over time. The measurements can be stopped once the current reaches steady state. When a circuit is driven with direct current (DC), there is no distinction between impedance and resistance; the latter can be thought of as impedance with zero phase angle. The current and/or the resistance (or impedance) can then be plotted versus time to provide a DC impedance plot as shown in FIG. 6. The different data points in the plot can be connected by a curve. Since this can be done for different DC signal voltages, in some instances, multiple DC impedance plots are generated for a single sample. In some instances, determining the impedance signature includes generating an AC impedance plot. An AC impedance plot can be generated by applying multiple AC signals across the sample and measuring the resulting impedance as shown in FIG. 7. The different AC signals can include a different amplitudes and/or different frequencies. An AC impedance plot can then be generated by plotting the real impedance versus frequency. Another type of impedance plot can then be generated by plotting the real impedance versus the imaginary impedance. The different data points in the plot can be connected by a curve. Because an AC impedance plot can be done for different AC signal frequencies or amplitudes, in some instances, multiple AC impedance plots are generated for a single sample. The above AC and DC impedance plots can be typical plots that use an y-axis and an x-axis or can be other plot types such as polar plots or circular plots.

In some instances, determining an impedance signature for a sample includes generating only DC impedance plots for the sample and can be as few as one DC impedance plot. In some instances, determining an impedance signature for a sample includes generating only AC impedance plots for the sample and can be as few as one AC impedance plot. In some instances, determining an impedance signature for a sample includes generating both one or more DC impedance plots and one or more AC impedance plot.

In some instances, the impedance signature includes a curve from each of the impedance plots generated for a sample. As will be described below, the impedance signature can be stored by a computer. Similarly, the above impedance plots and the resulting curve can be generated on a computer. Accordingly, when the impedance signature includes one or more of these curves the computer can store the curve. The curve can be stored as an a Nyquist or Bode (or both) impedance signatures in an Excel files, text file, Word file, digital format, and/or image format. Additionally or alternatively, in some instances, the impedance signature for a sample includes a mathematical representation of one or more of the curves generated for the sample. For instance, a mathematical representation can be generated by performing a curve fit on the curve itself or on the individual data points that make up the curve. The mathematical relationship that results from performing the curve fit can be stored by the computer. In some instance, only the variables of the mathematical relationship are stored by the computer.

Additionally or alternatively, in some instances, the impedance signature includes one or more mathematical features from one or more of the curves. For instance, the impedance signature for a sample can include one or more curvature values. Each curvature value represents the curvature of one of the one or more curves at a different location on the curve. Additionally or alternatively, in some instances, the impedance signature includes one or more curve values from one or more of the curves. Each curve value represents the value (the impedance, current, or resistance) of the curve at a different location along the curve. Additionally or alternatively, in some instances, the impedance signature includes the identity of one or more features from one or more of the curves. For instance, the impedance signature can include data that showing that a maximum or minimum occurs in the curve at a particular location along the curve and/or showing the value of the maximum or minimum in the curve.

A device according to FIG. 1A through FIG. 1C can be employed to generate the impedance signature as discussed above. For instance, a computer in electrical communication with the electrodes on the device can apply the AC signal(s) and/or the DC signal(s) that are used to generate the impedance signature to a sample located on the device as shown in FIG. 1B. Each of the above datum that defines an impedance signature can be stored in one or more field of a database according to FIG. 3.

At block 202, suitable data is identified. For instance, as is evident from the top row of FIG. 3, a database can be associated with a particular electrokinetic treatment functionality such as concentration of an agent at a central electrode 34. As is also evident from the first column of FIG. 3, database and/or equations can be associated with a particular selection of agent(s). Accordingly, each database can be associated with a particular functionality and agent(s). Further, as noted above, equations that express the relationship between impedance signature and parameters of the electrical signal can also be associated with a particular functionality and agent(s). As a result, the data (databases, equations, etc.) that is associated with the desired functionality and agent(s) is identified.

At block 204, the data identified in block 202 and the impedance signature determined at block 200 are used to identify the value of the parameters that are suitable for generating the electrical signal that is used during the electrokinetic treatment. For instance, at block 206, the impedance signature determined at block 200 is compared to the data identified at block 202. When the data identified in block 202 is in the form of a database, the impedance signature determined at block 200 can be compared to the impedance signatures in the database so as to identify one or more of the impedance signatures in the identified data. In some instances, the comparison is performed so as to identify the impedance signature in the database that is closest to the impedance signature determined in block 200.

The impedance signatures in the identified data that is closest to the impedance signature determined in block 200 can be identified by a manual visual inspection. For instance, the curves on one or more impedance plots generated for the sample can be visually compared to the curves on different impedance plots included in the identified data. The comparison can include looking for common features such as minima and maxima that occur at common locations (frequencies, impedance, time). Alternately, the identification of the closes impedance signature can be performed mathematically using data matching algorithms such as cross-correlation algorithms, complex sine correlation algorithms, Levenberg-Marquardt algorithm, and Pearson's chi-squared test. For instance, when matching curves, suitable algorithms include, but are not limited to, curve matching algorithms, cross correlation algorithms, complex sine correlation algorithms, Levenberg-Marquardt algorithm, and Pearson's chi-squared test. In some instances, these mathematical algorithms can be executed by the computer discussed below.

At block 208, the parameters that the identified data associates with the identified impedance signature are identified. For instance, when the impedance signature in the fifth row of the database shown in FIG. 3 is identified, the parameters labeled $V_{DC,2}$, $V_{AC,2}$, and $f_{AC,2}$ are identified.

When the identified data is in the form of mathematical equations, block 204 can be executed by plugging the impedance signature identified in block 200 into each of the equations identified in block 202. The equations are then solved to determine the value of each parameter. The calculated parameter values serve as the identified parameters.

At block 210, the identified parameters are used to perform the electrokinetic treatment of the sample. For instance, the electrical signal that is used during the electrokinetic treatment has the parameters identified at block 208. At block 212, the result of the electrokinetic treatment is used in an electrochemical analysis. For instance, the electrokinetically treated sample is used as the sample on which the electrochemical analysis is performed. Alternately, the electrokinetically treated sample is used to prepare the sample on which the electrochemical analysis is performed. For instance, the electrokinetically treated sample can be mixed with other liquids to prepare the sample on which the electrochemical analysis is performed.

Data for a database such as the above can be generated experimentally. For instance, an experimental sample having particular agent(s) can be obtained. The impedance signature for the experimental sample can be determined and the result entered into the fields of the database. Additionally, the experimental sample can be placed into contact with a device. The electrical signal applied to the electrodes of the device and the parameters changed such that a particular functionality is optimized. The impedance signature of the experimental sample and the parameters that provided the optimized result can be entered into a row of a database such as the database of FIG. 3. Other rows in the database can be filled out using other experimental sample that have the same agent(s) but different impedance signatures. As noted above, the data in the database can also be converted to mathematical equations.

Figure 5:
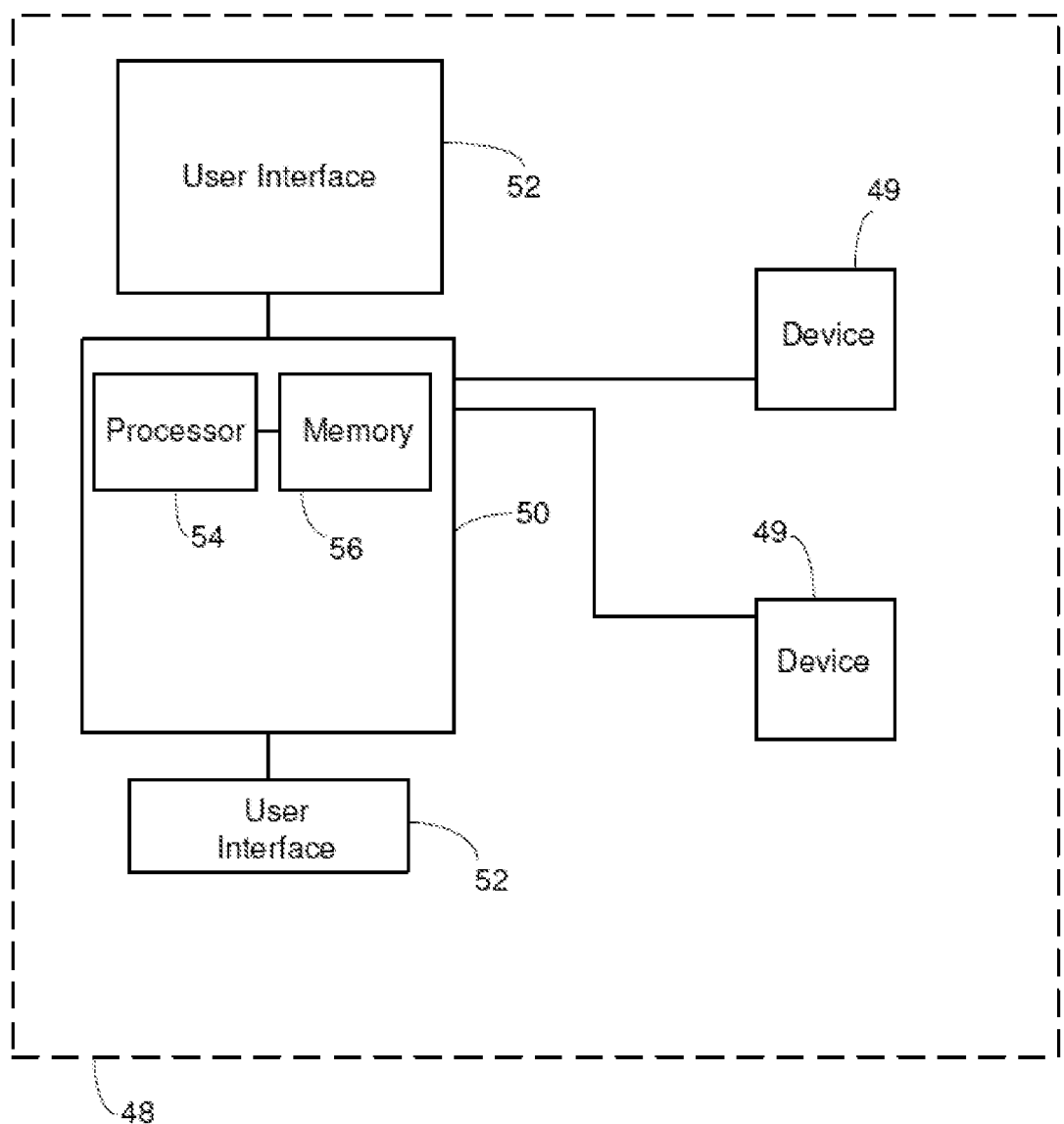
FIG. 5 illustrates a system that uses impedance signature data for a sample to identify the variables of an electrical signal that is to be applied to the sample during an electrokinetic treatment of the sample.

As discussed above, the devices and data disclosed above can be used in conjunction with a computer and the computer can perform a variety of the functions. FIG. 5 illustrates a system 48 that includes one or more of the above devices 49 and a computer 50. The computer is in electrical communication with one or more interfaces. Suitable user interfaces include, but are not limited to, keyboards, mice, and monitors.

The computer includes a processor in electrical communication with a computer readable medium such as a memory. The memory can be any memory device or combination of memory devices suitable for read and/or write operations. Suitable memory includes, but is not limited to, memory configured to store instructions and permanent data, as well as temporary memory configured to store temporary data and information. Thus, memory can includes comprise multiple memory devices such as static random access memory, flash memory, electrically erasable read-only memory, electrically programmable read-only memory, etc. Examples of the memory include, but are not limited to, hard drives, optical discs such as CDs, magnetic storage diskettes, Zip disks, magnetic tapes, RAMs, and ROMs.

Suitable processors include, but are not limited to, a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions attributed to the processor. A general-purpose processor may be a microprocessor, but in the alternative, the processor may include or consist of any conventional processor, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The computer is also optionally in electrical communication with one or more devices. The devices can include a device according to FIG. 1A through FIG. 1D and/or a device according to FIG. 2A and FIG. 2B. When the computer is in electrical communication with a device according to FIG. 1A through FIG. 1D, the computer can be configured to apply the electrical signal to the electrodes in the device so as to perform an electrokinetic treatment. Additionally, or alternatively, the computer can be configured to apply the electrical signal to the electrodes in the device so as to perform an electrochemical analysis of a sample, and optionally to analyze the results and output them to a user on one or more of the user interfaces and/or store the results in the memory. Additionally or alternately, the computer can be configured to apply the electrical signal to the electrodes in the device so as to generate data for identifying the impedance signature of a sample and optionally analyze the data so as to identify the impedance signature and output it to a user on one or more of the user interfaces and/or to store it in the memory.

An example of a computer configured to operate a device constructed according to FIG. 1A through FIG. 1B is the electrochemical sensor or EK control box sold by GeneFluidics, Inc. located in Irwindale, Calif., USA.

The data discussed above can be stored on the computer readable medium. The computer readable medium can also store computer executable instructions. The instructions on the computer readable medium can be executed by the processor. The instructions can be such that the processor and/or computer performs each of the acts described in the context of FIG. 4. In particular, in some instances, the processor and/or computer performs all of the steps in block 200 through block 212. In these instances, a user can employ a user input to input to the computer the desired functionality and agent(s) and the computer can employ this input to perform the remaining blocks. Alternately, the computer can perform a portion of the steps in block 200 through block 212. For instance, an operator can determine the impedance signature for a sample in accordance with block 200. The operator can then employ a user interface to input the impedance signature, agent(s), and desired functionality to the computer. The computer can then use this input to perform block 202 through block 208. The computer can then employ a user interface to output to the user the identified parameters. The user can then use these parameters to complete blocks 210 and optionally block 212. In this example, the computer does not operate one of the devices disclosed in the context of FIG. 1A through 2B. As a result, the communication between the devices and the computer is optional. Alternately, when the computer is in electrical communication with one of the devices and the computer has identified the parameters, the computer can optionally perform blocks 210 and/or block 212. As an alternative to the above functions being performed by a computer, they can all be performed by the operator.

Example 1

An example of an electrical signal that is suitable for concentrating bacteria in certain blood samples at the working electrode of a device constructed according to FIG. 1A through FIG. 1B is applied between the working electrode and the auxilliary electrode and includes a sinusoidal AC signal on top of a DC signal where the DC signal has a voltage in a range of 1V to −1V and the AC signal has a voltage in a range of 0.1 mV to 200 mV and a frequency in a range of 100 Hz to 1 MHz or the AC signal the AC signal has a voltage in a range of 50 mV to 1,000 mV and a frequency in a range of 50 Hz to 1 M Hz.

Example 2

An example of an electrical signal that is suitable for mixing the components of certain blood samples on the electrodes of a device constructed according to FIG. 1A through FIG. 1B is applied between the working electrode and the auxilliary electrode and is a sinusoidal AC signal on top of a DC signal where the DC signal has a voltage in a range of 1V to −1V and the AC signal has a voltage in a range of 0.1 mV to 200 mV and a frequency in a range of 100 Hz to 1 MHz or the AC signal has a voltage of 50 mV to 1,000 mV and a frequency in a range of 50 Hz to 1 M Hz.

Although FIG. 3 shows the database associating data in fields in the same row, the database can have other constructions. For instance, a suitable database can be inverted such that the data in the rows is located in columns. Further, the databases need not be limited to the data disclosed above. For instance, multiple databases according to FIG. 3 can be combined. For instance, a single database can be associated with a single functionality but can include data from different selections of agents. In these instances, when processing the data as described in the context of FIG. 4, the data that is associated with the desired agent(s) can be used and the data associated with other agent(s) can be excluded. Likewise, data associated with multiple functionalities can be included in a single database. In these instances, when processing the data as described in the context of FIG. 4, the data that is associated with the desired functionality can be used and the data associated with other functionalities can be excluded. Further, the data associated with multiple functionalities and multiple selections of agent(s) can be included in a single database. In these instances, when processing the data as described in the context of FIG. 4, the data that is associated with the desired functionality and selection of agent(s) can be used and the remaining data excluded.

Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

The invention claimed is:

1. A method, comprising:
using impedance signatures of different samples to identify an electrical signal that is appropriate for use in an electrokinetic treatment of each one of the samples, the electrical signals being identified such that different electrical signals are identified for different samples;
performing the electrokinetic treatment of each sample such that each sample is exposed to the electrical signal identified for that sample, the electrokinetic treatment employing one or more electrokinetic phenomena to cause movement of one or more agents within the sample relative to the sample; and
using each of the electrokinetically treated samples to generate an electrochemical sample; and
performing an electrochemical analysis on each of the electrochemical samples.

2. The method of claim 1, wherein one or more of the one or more electrokinetic phenomena are selected from a group consisting of dielectrophoretic phenomena, AC electroosmotic phenomena, AC electrothermal phenomena, and electrostatic phenomena.

3. The method of claim 1, wherein using the impedance signatures includes generating impedance plots for the samples.

4. The method of claim 3, wherein the impedance plots results from data generated by applying one or more DC signals to the samples.

5. The method of claim 3, wherein the impedance plots results from data generated by applying one or more AC signals to the samples.

6. The method of claim 3, wherein the determined impedance signatures include a curve from one or more of the impedance plots.

7. The method of claim 3, wherein the determined impedance signatures include a mathematical equation for a curve that fit data on one or more of the impedance plots.

8. The method of claim 3, wherein the determined impedance signatures include a numerical value that results from performing one or more mathematical calculations on data from one or more of the impedance plots.

9. The method of claim 8, wherein the mathematical calculation includes a determination of curvature.

10. The method of claim 3, wherein the determined impedance signatures include a feature that is present on a curve on one of the impedance plots.

11. The method of claim 1, wherein identifying the electrical signal for a sample includes comparing the impedance signature for the sample to data that indicates a relationship between impedance signatures and a value of one or more variables for the electrical signal.

12. The method of claim 11, wherein the comparison is performed so as to identify the values of the one or more variables for the electrical signal.

13. The method of claim 3, wherein the electrokinetic treatment is associated with a functionality selected from a group consisting of mixing one or more of the agents more uniformly within the sample, concentrating one or more of the agents at a location within the sample, and repelling one or more of the agents from a location within the sample.

14. The method of claim 1, wherein the electrokinetic treatment causes one of the agents to become more concentrated at a location within the sample.

15. The method of claim 1, wherein the electrokinetic treatment causes one of the agents to be repelled from a location within the sample.

16. The method of claim 1, wherein the electrokinetic treatment increases the uniformity at which one of the agents is mixed within the sample.

17. A non-transitory computer readable medium on which is stored computer readable data, the data comprising:
   electrokinetic treatment data indicating a relationship between an impedance signature of a sample and a value of one or more variables of an electrical signal to be applied to the sample during an electrokinetic treatment of the sample.

18. A non-transitory computer readable medium on which is located a computer readable program code, the computer readable program code adapted to be executed to implement a method for identifying signal variables, said method comprising:
   comparing an impedance signature for a sample to data that indicates a relationship between impedance signatures and values of one or more variables for an electrical signal to be applied to the sample during an electrokinetic treatment of the sample; and
   employing the comparison to identify the values of the variables.

19. The medium of claim 18, wherein comparing the impedance signature for the sample to the data includes selecting one impedance signature from among multiple alternative impedance signatures listed in the data.

20. The medium of claim 19, wherein employing the comparison to identify the values of the variables includes identifying the values of the one or more variables that the data associates with the identified impedance signature.

* * * * *